United States Patent [19]

Linder

[11] Patent Number: 4,512,967
[45] Date of Patent: Apr. 23, 1985

[54] CATIONIC TECHNETIUM COMPLEXES USEFUL AS RADIODIAGNOSTIC AGENTS

[75] Inventor: Karen E. Linder, Somerville, Mass.

[73] Assignee: E. I. Du Pont de Nemours and Compamy, Wilmington, Del.

[21] Appl. No.: 404,372

[22] Filed: Aug. 2, 1982

[51] Int. Cl.$^3$ .................. A61K 43/00; A61K 49/00
[52] U.S. Cl. ................ 424/1.1; 260/429 R; 260/440; 260/446; 424/9; 568/2; 568/8; 568/13; 568/14; 568/15; 568/16; 568/17
[58] Field of Search .............. 260/429 R, 440, 446; 568/2, 8, 13–17; 424/1, 1.5, 9

[56] References Cited

U.S. PATENT DOCUMENTS

| | | | |
|---|---|---|---|
| 2,587,805 | 3/1952 | Akobjanoff | 260/440 |
| 3,187,345 | 6/1965 | Burg et al. | 568/2 |
| 3,478,035 | 11/1969 | Barrett | 564/19 |
| 3,478,036 | 11/1969 | Winkelmann et al. | 564/19 |
| 3,798,241 | 3/1974 | Kagan et al. | 260/446 |
| 3,819,670 | 6/1974 | Kemp | 260/440 |
| 4,133,872 | 1/1979 | Schmidt-Dunker et al. | 424/1 |
| 4,247,534 | 1/1981 | Bevan | 424/1 |
| 4,338,248 | 7/1982 | Yokoyama et al. | 424/1 |
| 4,363,793 | 12/1982 | Blau et al. | 424/1 |
| 4,374,821 | 2/1983 | Glavan et al. | 260/429 R |
| 4,387,087 | 6/1983 | Deutsch et al. | 424/1.1 |

FOREIGN PATENT DOCUMENTS

0038756 10/1981 European Pat. Off. ............. 424/1

OTHER PUBLICATIONS

Friesen, D. K. et al., J. of Molecular Structure, 31 (1976), 77–95.
Communications to the Editor, J. Am. Chem. Soc., 1980, vol. 102, No. 22, 1980, pp. 6849–6851.
Zsuzsa Nagy-Magos et al., J. of Organometallic Chemistry, 171 (1979), 97–102.
Akhtar, M., et al., Inorganic Chemistry, vol. 11, No. 12, 1972, pp. 2917–2921.
Communications to the Editor, J. Am. Soc., 101, 1979, pp. 1053–1064.
Brown, L. D., et al., Inorganic Chemistry, vol. 17, No. 3, 1978, pp. 729–734.
Albright, J. O., et al., J. Am. Chem. Soc., 101, (1979), pp. 611–619.
Kyba, E. P., et al., J. Am. Chem. Soc., vol. 102, No. 23, 1980, pp. 7012–7014.
Butter, S. A., et al., J. Am. Chem. Soc., (1970), pp. 1411–1415.
Inoue, Y., et al., Bulletin of the Chem. Soc. of Japan, vol. 51(B), (1978), pp. 2375–2378.
Chatt, J., et al., J. Chem. Soc., (1961), pp. 896–904.
Mazzi, U., et al., Inorganic Chemistry, vol. 16, No. 5, (1977), pp. 1042–1048.
Chatt, J., et al., J. Chem. Soc., (1962), pp. 2545–2549.
Ferguson, J. E. et al., Aust. J. Chem., 1970, 23, 453–461.
King, R. B., Acc. Chem. Res. 1980, 13, pp. 243–248.
Wymore, C. E., et al., J. Inorg. Nucl. Chem., 1960, vol. 14, pp. 42–45.
Ferguson, J. E., et al., J. Inorg. Nucl. Chem., 1966, vol. 28, pp. 2293–2296.
Cooper, P., et al., J. Chem. Soc., (C) (1971), pp. 3031–3035.
Subramanian, Gopal, et al., Proceedings of the 28th Annual Meeting, Las Vegas, Jun. 16–19, 1982, vol. 22, No. 6, p. 51.
Deutsch, E. et al., Science, vol. 214, (1981), pp. 85–86.
Ferguson, J. E. et al., Chemistry and Industry, Nov. 22, 1958, p. 1555.
Curtis, N. F., Chemistry and Industry, May 24, 1958, pp. 525–626.
Communications to the Editor, J. Am. Chem. Soc., 97, (1975), pp. 1955–1956.
Bandoli, G. et al., J. C. S. Dalton, (1976), pp. 125–130.
Viard, B., J. Inorg. Nucl. Chem., 1977, vol. 39, pp. 1090–1092.
Ferguson et al., Chemistry and Industry, pp. 347–348.
Deutsch et al., J. Nucl. Med., vol. 22, (Oct. 1981): 897–907.

*Primary Examiner*—Christine M. Nucker
*Attorney, Agent, or Firm*—Sewall P. Bronstein; George W. Neuner

[57] ABSTRACT

A cationic lipophilic complex of technetium is disclosed wherein all of the coordination positions of the technetium atom are filled with a neutral donor atom having a pair of electrons available for forming a coordinate bond with technetium. The donor atoms are provided by target-seeking ligands or salts thereof, said ligands having the following structure of one of formulas I, II or III. Such complexes are useful for imaging heart and hepatobiliary tissues.

20 Claims, No Drawings

CATIONIC TECHNETIUM COMPLEXES USEFUL AS RADIODIAGNOSTIC AGENTS

FIELD OF THE INVENTION

The present invention relates to cationic radiodiagnostic agents and, in particular, to novel $^{99m}$Tc-labelled cationic radiodiagnostic agents, kits for preparing such $^{99m}$Tc-labelled cationic radiodiagnostic agents, and methods for using such $^{99m}$Tc-labelled cationic radiodiagnostic agents.

BACKGROUND OF THE INVENTION

Various complexes of monodentate and bidentate ligands with technetium have been made and studied. These complexes generally were made for use in studies to determine the various oxidation states of technetium and for other research regarding the structure of such complexes and metal-coordination chemistry. Such studies have been reported in, for instance, *Chemistry and Industry*, pp. 347–8 (Mar. 26, 1960); *J. Inorg. Nucl. Chem.*, Vol. 28, pp. 2293–96 (1966); *Aust. J. Chem.*, 23 pp. 453–61 (1970); *Inorganic Chem.*, Vol. 16, No. 5, pp. 1041–48 (1977); *J. Inorg. Nucl. Chem.*, Vol. 39, pp. 1090–92 (1977); and *J.C.S. Dalton*, pp. 125–30 (1976).

Recently, in a presentation to the American Pharmaceutical Association, E. A. Deutsch disclosed that certain complexes of DIARS, i.e.

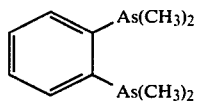

and Tc-99m, and certain complexes of DMPE, i.e. (CH$_3$)$_2$PCH$_2$CH$_2$P(CH$_3$)$_2$ and Tc-99m, may be useful as radiodiagnostic agents for myocardial or hepatobiliary imaging. [$^{99m}$Tc-(DMPE)$_2$Cl$_2$]+ and [$^{99m}$Tc-(DIARS)$_2$]+ were prepared by Deutsch by heating in an open flask a reaction mixture containing the appropriate hydrogen halide in aqueous alcohol solution, $^{99m}$Tc-sodium pertechnetate, and ortho-phenylenebis(dimethylarsine), i.e. DIARS, or bis-(1,2-dimethylphosphino)ethane, i.e. DMPE. The reaction was reported to take about 30 minutes. The labelled complex was then purified by chromatographic methods involving ion exchange columns.

The labelled complex produced according to the procedure of Deutsch has several practical disadvantages. The procedure requires handling several ingredients including an organic solvent to make the reaction mixture and then purifying the resulting radiolabelled complex by chromatography. Each of these handling steps can contaminate the system and final product. The purification step further requires additional time for preparation of the final product. These steps require a skilled technician and are performed at the site of use, just prior to use. Thus, a complex, time consuming chemical preparation is required during which sterility of ingredients and containers is difficult to maintain. Thus, to assure freedom from contamination, a final sterilization step is required, which further adds to preparation time. Because Tc-99m has a short half-life, lengthy preparation methods are undesirable. Thus, the complexity of the preparation, both with regard to maintaining sterile conditions and to purification of the $^{99m}$Tc-labelled complex make the Deutsch procedure undesirable.

It would be highly desirable to have a sterilized kit with all the necessary materials prepared by the manufacturer, to which only the Tc-99m need be added at the site of use to produce the desired labelled complex directly in high enough yield to obviate the need for purification. It would also be desirable for the kit materials to be in a closed container or vial, pre-sterilized, so that the only step to be performed at the site of use would be the addition of the radionuclide. To increase stability and shelf-life of the kit, it would be highly desirable that the materials be readily lyophilized, preferably from an aqueous solution.

By achieving the desirable features outlined above, a convenient-to-use heart imaging radiopharmaceutical agent would be provided that is capable of concentrating in healthy heart tissue to provide a negative image of an infarct, damaged or ischemic tissue.

A copending application, Ser. No. 311,770, filed Oct. 15, 1981 in the name of Vinayakam Subramanyam, which is hereby incorporated by reference, describes an acid salt of a mono or polydentate ligand that is water soluble, stable in a lyophilized state, and is capable of binding with Tc-99m to form a cationic complex. The acid salt may be generally represented by the formula:

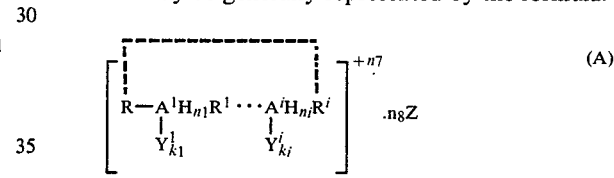

wherein:

i is an integer from 1 to 6;

R, R$^1$, R$^2$, R$^3$, R$^4$, R$^5$ and R$^6$ are each independently selected from hydrogen or substituted or unsubstituted alkyl, aryl, alkylaryl, arylalkyl, monocycloalkyl, polycycloalkyl, heterocyclic and carbocyclic groups, and R plus R$^i$ may be taken together to form a cyclic compound or separately to form a linear compound;

Y$^1$, Y$^2$, Y$^3$, Y$^4$, Y$^5$ and Y$^6$ are independently selected from substituted or unsubstituted alkyl, aryl, alkylaryl, arylalkyl, monocycloalkyl, polycycloalkyl, heterocyclic and carbocyclic groups;

A$^1$, A$^2$, A$^3$, A$^4$, A$^5$ and A$^6$ are the same or different neutral donor atoms, each having a free electron pair available for accepting a proton to provide a charged ligand or for complexing with Tc-99m or Tc-99 to form a cationic complex;

Z is preferably a parenterally acceptable anion;

k$_1$, k$_2$, k$_3$, k$_4$, k$_5$ and k$_6$ are each independently zero or one;

n$_1$, n$_2$, n$_3$, n$_4$, n$_5$ and n$_6$ are independently 0 or 1; and n$_7$ and n$_8$ are integers from 1 to 6 where $$n_7 = \sum_{i=1}^{6} n_i$$

and the charge represented by n$_8$Z is equal in magnitude and opposite in sign to +n$_7$; or

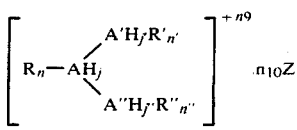

(B)

wherein:

R, R' and R" are independently selected from hydrogen or substituted or unsubstituted alkyl, aryl, alkylaryl, arylalkyl, monocylcloalkyl, polycycloalkyl, heterocyclic and carbocyclic groups;

A, A' and A" are independently selected from the group of neutral donor atoms having a pair of electrons available for accepting a proton to provide a charged ligand or for complexing with Tc-99m or Tc-99 to form a cationic complex;

j, j' and j" are independently 0 or 1;

n, n' and n" are independently the integer 1 or 2;

Z is the same as defined above;

$n_9$ and $n_{10}$ are integers selected from 1 to about 3, where $n_9 = j + j' + j''$ and the charge represented by $n_{10}Z$ is equal in magnitude and opposite in sign to $+n_9$.

These acid salts are normally solid compounds, water-soluble, readily lyophilized, and capable of reducing pertechnetate and binding with technetium to form stable cationic complexes.

SUMMARY OF THE INVENTION

The present invention provides a cationic lipophilic complex of technetium wherein all of coordination positions of the technetium atom are filled with a donor atom having a pair of electrons available for forming a coordinate bond with technetium to form a cationic complex, said donor atoms being provided by ligands or a salt thereof, said ligands having the following structure:

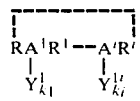

wherein i is an integer from 1 to 6;

R, $R^1$, $R^2$, $R^3$, $R^4$, $R^5$ and $R^6$ are each independently selected from hydrogen or substituted or unsubstituted alkyl, aryl, alkylaryl, arylalkyl, monocycloalkyl, polycycloalkyl, heterocyclic and carbocyclic groups, and R plus $R^i$ may be taken together to form a cyclic compound or separately to form a linear compound;

$Y^1$, $Y^2$, $Y^3$, $Y^4$, $Y^5$ and $Y^6$ are independently selected from hydrogen or substituted or unsubstituted alkyl, aryl, alkylaryl, arylalkyl, monocycloalkyl, polycycloalkyl, heterocyclic and carbocyclic groups;

$A^1$, $A^2$, $A^3$, $A^4$, $A^5$ and $A^6$ are the same or different donor atoms, each having a free-electron pair available for complexing with Tc-99m or Tc-99 to form a cationic comples; and $k_1, k_2, k_3, k_4, k_5$ and $k_6$ are each independently zero or one;

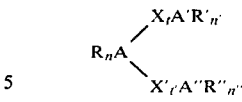

wherein:

R, R' and R" are independently selected from hydrogen or substituted or unsubstituted alkyl, aryl, alkylaryl, arylalkyl, monocylcloalkyl, polycycloalkyl, heterocyclic and carbocyclic groups;

X and X' are saturated or unsaturated alkyl groups; A, A' and A" are independently selected from the group of donor atoms having a pair of electrons available for complexing with Tc-99m or Tc-99 to form a cationic complex; t and t' are independently 0 or 1; n is 0, 1 or 2; and n' and n" are independently the integer 1 or 2; or

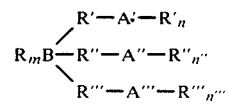

wherein

R, R', R" and R''' are independently selected from hydrogen or substituted or unsubstituted alkyl, aryl, alkylaryl, arylalkyl, monocylcloalkyl, polycycloalkyl, heterocyclic and carbocyclic groups;

A', A" and A''' are independently selected from the group of donor atoms having a pair of electrons available for complexing with TC-99m or TC-99 to form a cationic complex;

B is an atom selected from the group of donor atoms having a pair of electrons for complexing with Tc-99m or Tc-99, boron or from the elements listed in Group IV A of the periodic table (i.e C, Si, Ge, Sn, and Pb);

m is 0 or 1; and n', n" and n''' are independently the integer 1 or 2.

The R's in formulas I, II and III are preferably substituted or unsubstituted alkyl radicals having 1 to about 6 carbon atoms such as methyl, ethyl, etc., and the like, and substituted or unsubstituted aryl radicals such as benzyl, phenyl, etc., and the like. When more than one R group is attached to the same donor atom, the R groups so attached can be the same or different. Salts of the ligands of formulas I, II and III are preferably water soluble salts such as described by Subramanyam in copending Ser. No. 311,770, as aforesaid.

The cationic complexes of this invention, when radiolabelled are useful for radiodiagnostic tests in connection with myocardial and hepatobiliary tissues.

DETAILED DESCRIPTION OF THE INVENTION

A wide variety of monodentate and polydentate ligands are useful in the practice of this invention. Water-soluble ligand acid salts can be prepared from said ligands in accord with Subramanyam Ser. No. 311,770, as aforesaid. Typical examples of such ligands include, for instance, aryl compounds having arsenic, phosphorus, nitrogen, sulfur, oxygen, selenium, tellurium, or any combination of them, substituted ortho to each other. For example, o-phenylene compounds having the structure:

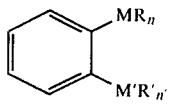

in which M and M' are arsenic, phosphorus, nitrogen, sulfur, oxygen, selenium, tellurium, or any combination of them, n and n' are independently 1 or 2 depending upon the particular donor atom used for M and M', and R and R' are independently hydrogen, or an organic group, preferably an alkyl group having 1 to 6 carbon atoms, an aryl group such as phenyl, or the like, and substituted such groups. When more than one R group is attached to the same donor atom, such R groups can be the same or different. Additional examples of suitable ligands include bidentate tetraethylene ligands of the formula:

in which M, M', R, and R' are as defined above, n and n' are 1 or 2 depending upon the particular M and M', and X and X' are independently selected from hydrogen, halide, or substituted or unsubstituted lower alkyl groups having 1 to about 6 carbon atoms. Further examples of suitable ligands include those having the formula:

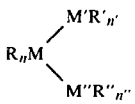

where M, M', R, and R', are as defined above, M" is independently selected from arsenic, phosphorous, nitrogen, sulfur, oxygen, selenium, and tellurium, n is 0 or 1, n' and n" are independently 0, 1 or 2, and R" is independently selected from hydrogen, halide or an organic radical, preferably an alkyl radical having 1 to about 6 carbon atoms, an aryl radical such as phenyl, or the like, and substituted such groups.

Throughout this application, whenever more than one R group is attached to the same donor atom, such R groups can be the same or different.

Particularly preferred ligands for the practice of this invention are the bis-dialkylphosphinoethanes, their substituted derivatives, and similar ligands, including, for example,
1,2-bis(dimethylphosphino)ethane,
1,2-bis(di(trifluoromethyl)phosphino)ethane,
1,2-bis(dimethylphosphino)-1,1-difluoroethane,
1,2-bis(dimethylphosphino)-1-fluoroethane,
1,2-bis(dimethylphosphino)propane,
1,2-bis(di(trifluoromethyl)phosphino)-1,1,2,2-tetrafluoroethane,
1,2-bis(di(trifluoromethyl)phosphino)propane,
2,3-bis(di(trifluoromethyl)phosphino)butane,
1,2-bis(di(trifluoromethyl)phosphino)butane,
1,3-bis(dimethylphosphino)butane,
1,3-bis(dimethylphosphino)propane,
1,3-bis(di(trifluoromethyl)phosphino)propane,
1,2-bis(dimethylphosphino)-1,1-dichloro-2,2-difluoroethane,
1,2-bis(diethylphosphino)ethane,
1,2-bis(diisopropylphosphino)ethane,
1,2-bis(dipropylphosphino)ethane,
1-dimethylphosphino-2-diisopropylphosphinoethane,
1,2-bis(diisobutylphosphino)ethane,
1-dimethylphosphino-2-dimethylarsinoethane,
and other similar compounds wherein the phosphorus is replaced by nitrogen, arsenic, sulfur, oxygen, selenium, tellurium, or any other atom having a free electron pair, and the like.

Other useful ligands include the alkylaminobis(difluorophosphine), i.e., $RN(PF_2)_2$, ligands and the like where R is an organic group, preferably an alkyl group having 1 to about 6 carbon atoms, an aryl group as phenyl, or the like, and substituted such groups; and the o-phenylene compounds such as, for example, orthophenylenebis(diarsine), orthophenylenebis(dimethylarsine), orthophenylenebis(diamine), orthophenylenebis(dimethylamine), orthophenylenebis(diphosphine), orthophenylenebis(dimethylphosphine), and the like.

Additional ligands suitable for use in the present invention are those described by Nozzo et al., in *J. Amer. Chem. Soc.*, 101, p. 3683 (1979) and by Wilson et al., *J. Amer. Chem. Soc.*, 100, p. 2269 (1978), which are hereby incorporated by reference.

Any donor element can be used in the ligand in accord with this invention provided that it is an atom having a free-electron pair available for accepting a proton to provide a charged ligand and further provided that it has the capability of complexing with technetium (Tc-99 or Tc-99m) to form a cationic complex in the presence of suitable anions. Suitable such elements include, for instance, phosphorous (P), arsenic (As), nitrogen (N), oxygen (O), sulfur (S), antimony (Sb), selenium (Se), tellurium (Te), and the like. Preferred elements are P and As.

The cationic technetium complexes of this invention that are useful for radiodiagnostic treatments are prepared by mixing the ligand and $^{99m}$Tc-pertechnetate in an aqueous or alcoholic solution having a basic pH, preferably 9.0 or more, and heating the mixture to form the cationic complex. Preferably, the ligand is provided as a lyophilized ligand acid salt as described by V. Subramanyam in copending application Ser. No. 311,770 and is contained in a sealed, sterilized vial prior to adding the pertechnetate. The pertechnetate solution can then be injected into the vial under aseptic conditions to maintain sterility. To obtain high yields, the vial is generally heated and maintained at an elevated temperature for sufficient time to form a complex of the ligand with technetium. The vial should preferably be heated to at least 80° C. for a suitable length of time, i.e. about 30 minutes or more at 80° C. Preferably, the vial is heated to 100° C. or more, and more preferably to a temperature in the range of from about 130° C. to about 150° C. At about 150° C., the reaction can be completed in about five to ten minutes, depending upon the choice and concentrations of the reactants. After cooling, the resulting radiopharmaceutical preparation may be adjusted for pH and is ready for use. Typically, when the pH is adjusted, it is adjusted into the range of from about 4.0 to about 9.0, and preferably to physiological pH.

It has been found that the preparation of the cationic technetium complex is improved by the addition of a polyhydroxy-compound to the reaction mixture. The use of the polyhydroxy-compound, for reasons not fully understood, results in a more consistent yield of the cationic technetium complex. Preferred polyhydroxy-compounds include, for example, Hetastarch (hydroxyethyl starch), mannitol, glycerol, D-mannose, sorbitol, and the like.

In order to form the cationic complexes of this invention a basic pH is desired for the complexing reaction to provide high yields of the desired complex. Preferably the pH is maintained at a pH of about 9 or more during the complexing reaction, and more preferably at a pH in the range of from about 10 to about 12.

To image the heart of a mammal, in-vivo, a radiopharmaceutical preparation in accord with the invention, having a suitable quantity of radioactivity for the particular mammal, is injected intravenously into the mammal. The mammal is positioned under a scintillation camera in such a way that the heart is covered by the field of view. High quality images of the heart are obtained analogous to those seen in clinical studies using Thallium-201.

In order to obtain high quality images the yield of radioactive labelled cationic technetium complex should preferably be greater than 70% after reconstituting the lyophilized mixture and labelling. Lower yields will result in poorer image quality and undesirable purification steps will be required to produce high quality images.

This invention will be further illustrated by the examples that follow:

EXAMPLE 1

Preparation of 1,2-Bis(dimethylphosphino)ethane-bis(tetrafluoroborate), i.e. $(DMPEH)_2{}^{2+}.2BF_4{}^-$ Place 210 mg of bis(dimethylphosphino)ethane in a 50 ml round-bottomed flask maintained under a nitrogen atmosphere, and dissolve it in 10 ml of ethanol. Add 0.5 ml of a 49% solution of tetrafluoroboric acid. After 15 minutes, remove the solvent in a rotary evaporator and recrystallize the product friom 15 ml of ethanol. Filter and dry under vacuum. 406 mg of a crystalline solid is obtained, which melts at 199.5°–210° C.

EXAMPLE 2

Preparation of 1,2-Bis(dimethylphosphino)ethane bis-bisulfate, i.e. $DMPEH_2{}^{2+}.2HSO^-{}_4$ or $DMPE.2H_2SO_4$ Dissolve 470 mg of DMPE in 10 ml of ethanol in a 50 ml round-bottomed flask maintained under a nitrogen atmosphere. From a glass syringe, add, with stirring, 0.34 ml of concentrated sulfuric acid. After 10 minutes, filter the precipitate and recrystallize it from 10 ml. of methanol. Filter and dry under vacuum. 920 mg of a crystalline solid is obtained, which melts at 135°–136.5° C. Structure and purity of the compound was confirmed by its infra-red and nuclear magnetic resonance spectra and elemental analysis.

EXAMPLE 3

Preparation of $[Tc(DMPE)_3]^+$

Add 10 ml. of degassed ethanol into a 25 ml. round-bottomed flask followed by 0.5 m mole (90 mg.) of $NH_4{}^{99}TcO_4$ (purified by recrystallization) and 2 m mole (300 mg) of Bis-(dimethylphosphino)ethane (DMPE). Reflux the solution under Argon atmosphere for 6 hours with stirring. Cool and add 0.5 m mole of sodium tetraphenylborate dissolved in 5 ml of ethanol to precipitate $[^{99}Tc(DMPE)_3]^+[BPh_4]^-$ as an off-white colored solid. Filter and wash the residue with water and ethanol. Dry in a vacuum desiccator. Yield is 90% of $[^{99}Tc(DMPE)_3]^+$ as determind by high pressure liquid chromatography (HPLC). Recrystallize the salt from acetonitrile.

The product is a white solid melting at >250° C. It moves toward a cathode (−dc) in an electrophoretic field indicating it is positively charged. Infra-red spectrum of the complex shows all absorptions characteristic of DMPE ligand and no Tc=0 stretch is seen. It is diamagnetic.

Elemental Analysis of the complex was done and the results calculated for $[Tc(DMPE)_3]^+[BPh_4]^-$ are given below:

|  | Calculated | Observed |
| --- | --- | --- |
| Carbon | 58.07 | 58.72 |
| Hydrogen | 7.89 | 7.98 |
| Phosphorus | 21.14 | 21.24 |

Specific activity of $^{99}Tc$-Liquid scintillation count Method.

Calculated for $[Tc(DMPE)_3]^+[BPh_4]^- = 1683$ $\mu Ci/\mu$ mole. Observed $= 1694 \pm 2$ $\mu Ci/\mu$ mole.

EXAMPLE 4

Alternative Preparation of $[Tc(DMPE)_3]^+$

Place 4 ml. of degassed ethanol in a 10 cc vial and add 0.2 ml. of 1N sodium hydroxide solution followed by 20 mg. of purified Tc-99 ammonium pertechnate $[NH_4{}^{99}TcO_4]$. Add 1 ml (800 mg) of DMPE and 50 mg. of sodium chloride. Dissolve 90 mg. of sodium dithionite $[Na_2S_2O_4]$ in 0.35 ml. of 1N sodium hydroxide solution and add to pertechnate solution. Let stand at room temperature for 15 minutes. Crude yield of desired compound is about 80% based on thin layer chromatography.

EXAMPLE 5

Preparation of $[^{99m}Tc(DMPE)_3]^+$

Dissolve 5 g mannitol and 115 mg DMPE-bis(bisulfate) of Example 2 (or an equivalent quantity of the bistetrafluoroborate salt of Example 1) in about 35 ml low-oxygen distilled water, and adjust the pH to 1.0 with 3N sulphuric acid. Under cover of nitrogen and with stirring add low-oxygen distilled water gravimetrically to a solution weight of 50 g. Dispense 1 ml of this solution into each of several 10 cc vials. Freeze-dry in keeping with procedures well-known to those skilled in the art, stoppering under nitrogen. Reconstitute each of the vials with 1 ml of physiological saline containing about 10–20 mCi of $^{99m}Tc$-pertechnetate, and add 0.15 ml 1N sodium hydroxide solution. The pH is about 12. Autoclave for 30 minutes at 135° C. TLC analyses show almost 95% yield of $[^{99m}Tc(DMPE)_3]^+$, the structure and charge of the complex having been confirmed by elemental analysis, infra-red and nuclear magnetic resonance spectra of the Tc-99 analogue, and by electrophoretic mobility.

EXAMPLE 6

Preparation of $^{99m}Tc[(1\text{-dimethylarsino})(2\text{-dimethylphosphino})ethane_3]^+ (^{99m}Tc(ASP)_3{}^+)$, i.e.

1.0 ml of well degassed normal saline (0.15M NaCl), containing 50 mCi of $^{99m}Tc$-pertechnetate is dispensed into a nitrogen purged, crimp sealed 10 cc vial. 10 $\mu l$ of 1-dimethylarsino-2-dimethylphosphinoethane is added via syringe, and the vial boiled for 45 minutes in a 100° C. water bath. Analysis by thin layer chromatography shows yields of 79–81% labeled product, $^{99m}Tc(ASP)_3{}^+$.

EXAMPLE 7

Preparation of $^{99m}Tc(bis(1,2\text{-diethylphosphino})ethane)_3{}^+$, i.e. $^{99m}Tc(DEPE)_3{}^+$ Under nitrogen with stirring, 30 μl of 1,2-diethylphosphinoethane is added to 20 ml of 95% ethanol. The solution is adjusted to pH 12.3 with 0.25N solium hydroxide and 0.5 ml of solution dispensed into each of several $N_2$ purged crimp sealed vials. 0.5 ml of normal saline, containing 40–60 mCi of $^{99m}Tc$-pertechnetate solution is added to each vial. Labelling, by heating in an autoclave for 40 minutes at 150° C. yields 30 to 45% labelled product, $^{99m}Tc(DEPE)_3{}^+$, as analyzed by high pressure liquid chromatography.

EXAMPLE 8

Preparation of $^{99m}Tc(bis(1,2\text{-dimethylphosphino})propane)_3{}^+$, i.e. $^{99m}Tc(DMPP)_3{}^+$ Under nitrogen, with stirring, 40 μl of bis(1,2-dimethylphosphino)propane is added to 20 ml of 95% ethanol. 2 ml of this solution is dispensed into each of several nitrogen purged, crimp sealed 10 cc vials, and 10 μl of 0.25N sodium hydroxide added to each vial. 0.5 ml of normal saline containing 20–40 mCi of $^{99m}Tc$-pertechnetate solution is added to each vial. Labelling by heating in an autoclave for 40 minutes at 150° C. yields 30% labelled product, $^{99m}Tc(DMPP)_3{}^+$, as analyzed by high pressure liquid chromatography.

EXAMPLE 9

Imaging of Rabbit Heart Using Tl-201 (Prior Art)

2 mCi of Thallium-201 (as thallous chloride in physiological saline containing 0.9% benzyl alcohol) is injected intravenously into a 2.5 Kg male New Zealand Albino rabbit. The rabbit is positioned under a Searle Pho-Gamma scintillation camera in such a way that the heart and lung area are covered by the field of view. Approximately 10 minutes after injection, sufficient counts are accumulated to produce an image of the heart analogous to that seen in clinical studies of humans.

EXAMPLE 10

Imaging of Rabbit Heart Using $^{99m}Tc$-labelled Products with ≧80% Yield of Desired Labelled Complex Greater than 1 mCi of the $^{99m}Tc$-labelled product of Example 5 or Example 6 is injected into a rabbit and imaged as in Example 9. The quality and appearance of the heart image is similar to that obtained in Example 9.

EXAMPLE 11

Imaging of Baboon Heart Using $^{99m}Tc$-labelled Products with ≧80% of Desired Labelled Complex Greater than 10 mCi of the $^{99m}Tc$-labelled product of Example 5 or Example 6 is injected intravenously into an adult baboon positioned under a scintillation camera as was the rabbit in Example 10. Excellent quality images of the heart are obtained, which are equivalent to those characteristically obtained with Tl-201 in humans.

This invention has been described in detail with particular reference to the preferred embodiments thereof. However, it will be appreciated that those skilled in the art, upon reading this disclosure, may make modifications and improvements within the spirit and scope of the invention.

I claim:

1. A cationic lipophilic complex of technetium wherein all of the coordination positions of the technetium atom are filled with a donor atom having a pair of electrons available for forming a coordinate bond with technetium to form said cationic complex, said donor atoms being provided by ligands or salts thereof, said ligands having the following structure:

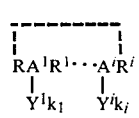
(A)

wherein:
i is an integer from 1 to 6;
R, $R^1$, $R^2$, $R^3$, $R^4$, $R^5$ and $R^6$ are each independently selected from hydrogen or substituted or unsubstituted alkyl, aryl, alkylaryl, arylalkyl, monocycloalkyl, polycycloalkyl, heterocyclic and carbocyclic groups, and R plus $R^i$ may be taken together to form a cyclic compound or separately to form a linear compound;
$Y^1$, $Y^2$, $Y^3$, $Y^4$, $Y^5$ and $Y^6$ are independently selected from hydrogen or substituted or unsubstituted alkyl, aryl, alkylaryl, arylalkyl, monocycloalkyl, polycycloalkyl, heterocyclic and carbocyclic groups;
$A^1$, $A^2$, $A^3$, $A^4$, $A^5$ and $A^6$ are each, independently, a donor atom having a free electron pair available for complexing with Tc-99m or Tc-99 to form a cationic complex; and
$k_1$, $k_2$, $k_3$, $k_4$, $k_5$ and $k_6$ are each independently zero or one;

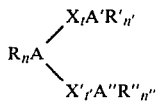
(B)

wherein:
R, R' and R" are independently selected from hydrogen or substituted or unsubstituted alkyl, aryl, alkylaryl, arylalkyl, monocylcloalkyl, polycycloalkyl, heterocyclic and carbocyclic groups;
X and X' are saturated or unsaturated alkyl groups; A, A' and A" are independently selected from the group of donor atoms having a pair of electrons available for complexing with Tc-99m or Tc-99 to form a cationic complex; t and t' are independently 0 or 1; n is 0, 1 or 2; and n' and n" are independently the integer 1 or 2; or

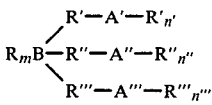

wherein
R, R', R" and R'" are independently selected from hydrogen or substituted or unsubstituted alkyl, aryl, alkylaryl, arylalkyl, monocylcloalkyl, polycycloalkyl, heterocyclic and carbocyclic groups;

A', A" and A''' are independently selected from the group of donor atoms having a pair of electrons available for complexing with Tc-99m or Tc-99 to form a cationic complex;

B is an atom selected from the group of donor atoms having a pair of electrons available for complexing with Tc-99m or Tc-99, boron, or from the elements of Group IV A of the periodic table;

m is 0 or 1; and n', n" and n''' are independently the integer 1 or 2.

2. The complex of claim 1 wherein A is selected from the group consisting of P, As, N, O, S, Sb, Se and Te.

3. The complex of claim 1 wherein at least one of the donor atoms are provided by a ligand having the formula:

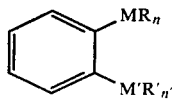

or salts thereof wherein M and M' are arsenic, phosphorus, nitrogen, sulfur, oxygen, selenium, tellurium, or any combination of them, n and n' are independently 1 or 2 depending upon the particular M and M', and R and R' are independently hydrogen, an alkyl group having from 1 to about 6 carbon atoms, or an aryl group.

4. The complex of claim 1 wherein at least one of the donor atoms are provided by a ligand having the formula:

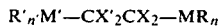

or salts thereof wherein M and M' are arsenic, phosphorus, nitrogen, sulfur, oxygen, selenium, tellurium, or any combination of them, n and n' are independently 1 or 2 depending on the particualr M and M', R and R' are independently hydrogen, an alkyl group having from 1 to about 6 carbon atoms, or an aryl group, and X and X' are independently selected from hydrogen, halide, or substituted or unsubstituted lower alkyl groups having 1 to about 6 carbon atoms.

5. The complex of claim 1 wherein at least one of the donor atoms are provided by a ligand having the formula:

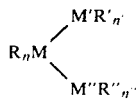

or salts thereof wherein M, M' and M" are independently selected from arsenic, phosphorous, nitrogen, sulfur, oxygen, selenium, and tellurium, n is 0 or 1 and n' and n" are independently 0, 1 or 2 depending upon the particular M, M' and M" used, and R, R' and R" are independently selected from hydrogen, halide, an alkyl group having 1 to about 6 carbon atoms, or an aryl group.

6. The complex of claim 1 consisting of a technetium atom and three ligands, each having the formula:

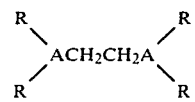

wherein each A is independently P or As; and each R is independently H, a lower alkyl group having from 1 to about 6 carbon atoms, or phenyl.

7. The complex of claim 1 consisting of a technetium atom and three ligands each having the formula:

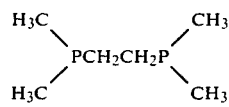

8. The complex of claim 1 consisting of a technetium atom and three ligands each having the formula:

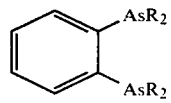

wherein R is H or a lower alkyl group having 1 to about 6 carbon atoms.

9. A method for making a cationic complex comprising Tc-99m for radioscintigraphic imaging, said method comprising admixing, in a suitable solvent at a basic pH, $^{99m}$Tc pertechnetate and a ligand or a salt thereof, said ligand having the formula:

(A)

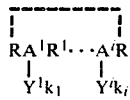

wherein:

i is an integer from 1 to 6;

R, $R^1$, $R^2$, $R^3$, $R^4$, $R^5$ and $R^6$ are each independently selected from hydrogen or substituted or unsubstituted alkyl, aryl, alkylaryl, arylalkyl, monocycloalkyl, polycycloalkyl, heterocyclic and carbocyclic groups, and R plus $R^i$ may be taken together to form a cyclic compound or separately to form a linear compound;

$Y^1$, $Y^2$, $Y^3$, $Y^4$, $Y^5$ and $Y^6$ are independently selected from hydrogen or substituted or unsubstituted alkyl, aryl, alkylaryl, arylalkyl, monocycloalkyl, polycycloalkyl, heterocyclic and carbocyclic groups;

$A^1$, $A^2$, $A^3$, $A^4$, $A^5$ and $A^6$ are each, independently a donor atoms having a free-electron pair available for complexing with Tc-99m or Tc-99 to form a cationic complex; and $k_1$, $k_2$, $k_3$, $k_4$, $k_5$ and $k_6$ are each independently zero or one;

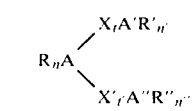

wherein:

R, R' and R" are independently selected from hydrogen or substituted or unsubstituted alkyl, aryl, alkylaryl, arylalkyl, monocylcloalkyl, polycycloalkyl, heterocyclic and carbocyclic groups;

X and X' are saturated or unsaturated alkyl groups; A, A' and A" are independently selected from the group of donor atoms having a pair of electrons available for complexing with Tc-99m or Tc-99 to form a cationic complex; t and t' are independently 0 or 1; n is 0, 1 or 2; and n' and n" are independently the integer 1 or 2; or

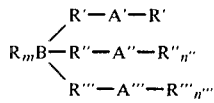

wherein

R, R', R" and R"' are independently selected from hydrogen or substituted or unsubstituted alkyl, aryl, alkylaryl, arylalkyl, monocycloalkyl, polycycloalkyl, heterocyclic and carbocyclic groups;

A', A" and A"' are independently selected from the group of donor atoms having a pair of electrons available for complexing with Tc-99m or Tc-99 to form a cationic complex;

B is an atom selected from the group of donor atoms having a pair of electrons available for complexing with Tc-99m or Tc-99, boron, or from the elements of Group IV A of the periodic table;

m is 0 or 1; and n', n" and n"' are independently the integer 1 or 1; thus forming the cationic complex.

10. The method of claim 9 wherein the pH of the solution is maintained at 9 or more during the complexing reaction.

11. The method of claim 9 where A is selected from the group consisting of P, As, N, O, S, Sb, Se and Te.

12. The method of claim 9 wherein at least one of the donor atoms are provided by a ligand having the formula:

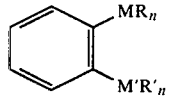

or salts thereof wherein M and M' are arsenic, phosphorus, nitrogen, sulfur, oxygen, selenium, tellurium, or any combination of them, n and n' are independently 1 or 2 depending upon the particular M and M', and R and R' are independently hydrogen, an alkyl group having from 1 to about 6 carbon atoms, or an aryl group.

13. The method of claim 9 wherein at least one of the donor atoms are provided by a ligand having the formula:

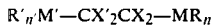

or salts thereof wherein M and M' are arsenic, phosphorus, nitrogen, sulfur, oxygen, selenium, tellurium, or any combination of them, n and n' are independently 1 or 2 depending on the particular M and M', R and R' are independently hydrogen, an alkyl group having from 1 to about 6 carbon atoms, or an aryl group, and X and X' are independently selected from hydrogen, halide, or substituted or unsubstituted lower alkyl groups having 1 to about 6 carbon atoms.

14. The method of claim 9 wherein at least one of the donor atoms are provided by a ligand having the formula:

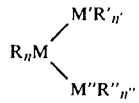

or salts thereof wherein M, M' and M" are independently selected from arsenic, phosphorous, nitrogen, sulfur, oxygen, selenium, and tellurium, n is 0 or 1 and n' and n" are independently 1 or 2 depending upon the particular M, M' and M" used, and R, R' and R" are independently selected from hydrogen, halide, an alkyl group having 1 to about 6 carbon atoms, or an aryl group.

15. The method of claim 9 wherein a technetium atom and three ligands or salts thereof, each ligand having the formula:

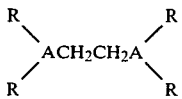

wherein each A is independently P or As; and each R is independently H a lower alkyl group having from 1 to about 6 carbon atoms, or phenyl.

16. The method of claim 9 wherein said complex a technetium atom and three ligands or salts thereof, each ligand having the formula:

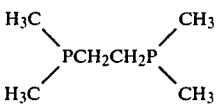

17. The method of claim 9 wherein said complex comprises a technetium atom and three ligands or salts thereof, each ligand having the formula:

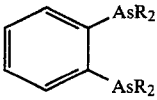

wherein R is H or a lower alkyl group having 1 to about 6 carbon atoms.

18. The method of claim 9 further comprising heating the admixture to at least 80° C.

19. The method of claim 9 wherein the pH is maintained in the range of from about 10 to about 12 during the reaction.

20. A method for visualizing the heart or the hepatobiliary system of a mammal by radioscintigraphy, said method comprising injecting into the mammal the cationic complex of any of claims 1 through 8, and scanning the mammal using radioscintigraphic imaging apparatus.

* * * * *